United States Patent [19]

Kishimoto et al.

[11] Patent Number: 4,904,587
[45] Date of Patent: Feb. 27, 1990

[54] PRODUCTION OF D-RIBOSE

[75] Inventors: Katsumitsu Kishimoto; Kazuhiko Kintaka, both of Hikari; Nobuhiro Uchiyama, Kumage, all of Japan

[73] Assignee: Takeda Chemical Industries, Ltd., Osaka, Japan

[21] Appl. No.: 243,041

[22] Filed: Sep. 12, 1988

[30] Foreign Application Priority Data

Sep. 10, 1987 [JP] Japan ................................ 62-226997

[51] Int. Cl.$^4$ .......................... C12P 19/04; C12R 1/07; C12N 1/20
[52] U.S. Cl. .................................... 435/105; 435/832; 435/252.5
[58] Field of Search ......................... 435/105, 832, 253

[56] References Cited

U.S. PATENT DOCUMENTS 3,919,046 11/1975 Sasajima et al. ..................... 435/105
3,970,522 7/1976 Sasajima et al. ..................... 435/105

OTHER PUBLICATIONS

*Chemical Abstracts,* Mochizuki et al.; Jan. 3, 1977, vol. 86, No. 1; p. 320, #3587(h).
*Chemical Abstracts,* Kenichi et al.; Dec. 20, 1976; vol. 85; No. 25, p. 405, #190748(a).
*Chemical Abstracts,* Yoneda et al.; Mar. 2, 1970; vol. 72; No. 9, p. 277, #41774(k).
*Chemical Abstracts,* Kintaka et al.; Apr. 13, 1987; vol. 106, No. 15, p. 503, #118148(q).

*Primary Examiner*—Ronald W. Griffin
*Assistant Examiner*—Pamela S. Webber
*Attorney, Agent, or Firm*—Wenderoth, Lind & Ponack

[57] ABSTRACT

By cultivating a D-ribose-producing microorganism of the genus Bacillus in a medium containing nutrients necessary for its growth, wherein the concentrations of L-tryptophan and L-tyrosine in the medium are controlled at 3 μg/ml or less and 10 μg/ml or less, respectively. D-ribose is produced in a good yield and the by-production of gluconic acid is efficiently suppressed.

7 Claims, No Drawings

PRODUCTION OF D-RIBOSE

This invention relates to a fermentative process for production of D-ribose.

D-Ribose as a component unit of ribonucleic acid occurs in all living matter, and ribitol, a reduced form derivative thereof, occurs as a component unit of vitamin $B_2$ and teichoic acid which is a building block of the cell wall. Thus, D-ribose is a physiologically important substance.

Meanwhile, D-ribose has been used as a starting material in the synthesis of vitamin $B_2$ and more recently has been much utilized as a starting material for synthetic production of nucleotide condiments. Therefore, it is of great commercial significance to produce D-ribose at low cost and in large quantities.

As methods for production of D-ribose, there are known the extractive process for isolation from natural resources, the synthetic processes starting with furan, glucose, etc. and the fermentative processes utilizing microorganisms (Japanese Patent Publication No. 7948/1972 and Japanese Unexamined Patent Application Laid-open No. 20388/1974).

The hitherto-known production processes referred to above invariably have drawbacks, some involving a complicated series of production steps, other requiring the use of costly starting materials and still others being conducive to only poor yields due to by-production of gluconic acid, and none can be considered to be really satisfactory from the commercial point of view.

The intensive research by the present inventors for establishing a process for producing D-ribose in high yields by a fermentation technique using a bacterium of the genus Bacillus revealed that in the fermentation process using a D-ribose-producing strain of the genus Bacillus, the production of D-ribose can be markedly increased by controlling the amounts of aromatic amino acids available in the culture medium. This invention is based on the above and subsequent research findings.

Thus, this invention relates to a process for producing D-ribose comprising cultivating a D-ribose-producing strain of the genus Bacillus in a medium containing nutrients necessary for its growth, wherein the concentrations of L-tryptophan and L-tyrosine in the medium are controlled at 3 µg/ml or less and 10 µg/ml or less, respectively.

The D-ribose-producing strain of the genus Bacillus which is employed in this invention includes various strains of *Bacillus pumilus* and *Bacillus subtilis*, such as, for example, *Bacillus pumilus* No. 503 (IFO 12600, ATCC 21356), No. 537 (IFO 12601, ATCC 21357), No. 558 (IFO 12602, ATCC 21358), No. 716 (IFO 13322, FERM BP-812, ATCC 21951), No. 911 (IFO 13566, FERM P-2260, ATCC 31095), No. 1027 (IFO 13585, FERM P-2466, ATCC 31098) and No. 1083 (IFO 13620, FERM P-2832, ATCC 31093), and *Bacillus subtilis* No. 429 (IFO 12603, ATCC 21359), No. 483 (IFO 12604, ATCC 21360), No. 608 (IFO 13323, FERM P-1490, ATCC 21952), No. 957 (IFO 13565, FERM P-2259, ATCC 31096), No. 941 (IFO 13573, FERM P-2360, ATCC 31097), No. 1054 (IFO 13586, FERM P-2467, ATCC 31091), No. 1067 (IFO 13588, FERM P-2468, ATCC 31092) and No. 1097 (IFO 13621, FERM P-2833, ATCC 31094).

The IFO numbers in the above list of microorganisms represent the accession numbers at Institute for Fermentation, Osaka (IFO, 17-85, Jusohonmachi 2-chome, Yodogawa-ku, Osaka 532, Japan); the FERM numbers represent the accession numbers at Fermentation Research Institute of the Agency of Industrial Science and Technology, the Ministry of International Trade and Industry (FRI, 1-3, Higashi 1-chome, Tsukuba, Ibaraki 305, Japan); and the ATCC numbers represent the accession numbers at The American Type Culture Collection (ATCC, U.S.A., 12301 Parklawn Rockville, Md. 20852 U.S.A).

Referring to the above-mentioned microorganisms, the bacteriological characteristics of *Bacillus pumilus* and *Bacillus subtilis* are the same as those described on pages 529–534 on Bergey's Manual of Determinative Bacteriology, the Eighth Edition. However, the above list includes mutants which are defective of sporulating ability owing to mutagenic treatment.

The microorganisms employed in this invention include microorganisms of the genus Bacillus which require aromatic amino acids (L-tyrosine, L-tryptophan and L-phenylalanine) for growth and microorganisms of the genus Bacillus which are deficient in at least one of transketolase and D-ribose-5-phosphate-3-epimerase, inclusive of mutants of such microorganisms which are deficient in sporulating ability and those which have high 2-deoxy-D-glucose-oxidizing activity. These microorganisms require said aromatic amino acids for growth but if such aromatic acids are available in excess, they not only produce and accumulate D-ribose but also produce large amounts of gluconic acid as a by-product after they have attained sufficient growth. In accordance with this invention, the concentrations of aromatic amino acids in the medium are controlled at 3 µg/ml or less, preferably 1 µg/ml or less, for L-tryptophan, 10 µg/ml or less, preferably 5 µg/ml or less, for L-tyrosine, and further 50–400 µg/ml, preferably 100–200 µg/ml, for L-phenylalanine during the fermentation, whereby the formation of said by-product is inhibited.

Thus, in this invention, the microorganism is fully grown in a medium containing nutrients necessary for its growth and, then, the concentrations of L-tyrosine, L-tryptophan and L-phenylalanine are controlled within the aforementioned ranges.

Generally in the mass production of D-ribose by a fermentation technique, cultivation of the microorganism is carried out in two stages, seed culture and main culture. In this invention, it is not always necessary to control the concentrations of the aforesaid aromatic amino acids during seed culture but all that is necessary is to control the concentrations during main culture.

For accomplishing such control, one may use a medium which already contains said aromatic amino acids within the aforesaid concentration ranges or add said aromatic amino acids to a medium free of such amino acids at levels required to establish the necessary concentrations.

For preparation of the medium, various carbon sources and nitrogen sources are used as nutrient sources. As specific examples of such carbon sources, there may be mentioned D-glucose, D-fructose, D-mannose, D-sorbitol, D-mannitol, sucrose, molasses, starch hydrolyzate, starch, acetic acid, ethanol and so on.

Examples of said nitrogen sources include various organic nitrogenous materials such as corn steep liquor, cottonseed cake, yeast extract, dried yeast, fishmeal, meat extract, peptone, casamino acid, etc., inorganic nitrogen compounds such as aqueous ammonia, ammonia gas, ammonium sulfate, ammonium nitrate, ammonium chloride, ammonium carbonate, ammonium phosphate, sodium nitrate, etc. and organic nitrogen compounds such as urea, amino acids and so on. Particularly useful is corn steep liquor.

It is especially preferable that corn steep liquor which does not contain L-tryptophan and contains about 0.04% (w/w) or less of L-tyrosine and about 0.5–0.7% (w/w) of L-phenylalanine based on the corn steep liquor with water content of 50% is added at the level of about 2 to 2.5% (w/w) based on the total amount of the medium as a nitrogen source.

The corn steep liquor mentioned above can be prepared, for example, by the process described in Reference example.

In addition to such carbon and nitrogen sources, various metals, vitamins and amino acids which are necessary for growth of the microorganism are added in appropriate amounts to the medium.

While the cultural conditions, such as the cultivation temperature, medium pH, cultivation time, etc., are not limited, the cultivation temperature is generally about 18°–45° C. and preferably about 25°–40° C. Regarding the concentrations of said aromatic amino acid, when the concentration of L-tyrosine is not less than about 8 μg/ml and that of L-phenylalanine is not less than about 300 μg/ml, the preferred cultivation temperature is about 35° C. or higher. The pH of the medium may range generally from about 4.5 to 9 and preferably from about 5.5 to 8. The cultivation time is generally about 18 to 180 hours and preferably about 36 to 120 hours. The D-ribose produced and accumulated in the culture broth can be harvested by the known procedure for recovery of D-ribose. For example, the fermentation broth is filtered or centifuged to remove the cells and the filtrate or supernatant is subjected to treatments with activated carbon and ion exchange resin for decoloration and desalting, followed by concentration. Then, an organic solvent such as ethanol is added to the concentrate for crystallization. Where the broth contains carbohydrates concomitantly with the desired product D-ribose, the broth is treated with glucose oxidase or a strain of microorganism which does not utilize yeast or D-ribose but utilizes the carbohydrates to remove the carbohydrates.

By growing a D-ribose-producing microorganism of the genus Bacillus while the available amounts of aromatic amino acids are controlled to favor the production and accumulation of D-ribose, the by-production of gluconic acid can be suppressed and the output of D-ribose increased. Furthermore, because the output of gluconic acid is small, the separation and removal of gluconic acid is facilitated.

The following experimental, working and reference examples are intended to illustrate the invention in further detail and should by no means be construed as limiting the scope of the invention.

It should be understood that all percents (%) mentioned in connection with medium composition are weight/volume percents (w/v %) unless otherwise indicated in the following Examples.

EXPERIMENTAL EXAMPLE

In the procedure described in Example 1 which appears hereinafter, corn steep liquors (hereinafter CSL) of various amino acid compositions (Lot Nos. 1 to 4) shown in Table 1 were used in the main medium and the outputs of D-ribose and gluconic acid were investigated with or without addition of aromatic amino acids to the medium. The results are shown in Table 2.

The outputs of D-ribose were determined by the orcinol method described in Methods in Carbohydrate Chemistry, Vol. 1, page 484, 1962.

TABLE 1

| Amino acid | CSL lot (% w/w)* | | | |
|---|---|---|---|---|
| | No. 1 | No. 2 | No. 3 | No. 4 |
| L-Aspartic acid | 0.038 | 0.04 | 0.052 | 0.068 |
| L-Threonine | 0.682 | 0.35 | 0.47 | 0.527 |
| L-Serine | — | — | — | — |
| L-Glutamic acid | 0.106 | 0.19 | 0.187 | 0.186 |
| L-Proline | 0.632 | 0.764 | 0.754 | 0.785 |
| L-Glycine | 0.265 | 0.35 | 0.351 | 0.367 |
| L-Alanine | 2.060 | 2.34 | 2.49 | 2.577 |
| L-Cystine | 0.301 | 0.145 | 0.31 | 0.401 |
| L-Valine | 0.563 | 0.620 | 0.680 | 0.690 |
| L-Methionine | 0.288 | 0.346 | 0.355 | 0.377 |
| L-Isoleucine | 0.317 | 0.384 | 0.392 | 0.408 |
| L-Leucine | 1.267 | 1.452 | 1.460 | 1.498 |
| L-Tyrosine | 0.412 | 0.04 | 0.021 | trace |
| L-Phenylalanine | 0.546 | 0.647 | 0.632 | 0.609 |
| L-Histidine | 0.002 | 0.005 | 0.005 | trace |
| L-Lysine | 0.106 | 0.05 | 0.110 | 0.159 |
| L-Arginine | 0.009 | 0.001 | 0.001 | trace |
| L-Tryptophan | 0 | 0 | 0 | 0 |

*Amount of amino acids in CSL containing about 50% (w/w) of water.

TABLE 2

| Run | Lot of CSL used (from Table-2) | Amounts (mg/l) of aromatic amino acids fed to medium containing 26 g/l of CSL | | Amount of amino acid added (mg/l) | Output of D—ribose (mg/ml) | Output of gluconic acid (mg/ml) |
|---|---|---|---|---|---|---|
| 1 | No. 1 | L-Tryptophan | 0 | — | 65 | 40 |
| | | L-Tyrosine | 107 | | | |
| | | L-Phenylalanine | 142 | | | |
| 2 | No. 2 | L-Tryptophan | 0 | — | 75 | 18 |
| | | L-Tyrosine | 10 | | | |
| | | L-Phenylalanine | 168 | | | |
| 3 | No. 3 | L-Tryptophan | 0 | — | 85 | 6 |
| | | L-Tyrosine | 5 | | | |
| | | L-Phenylalanine | 159 | | | |
| 4 | No. 4 | L-Tryptophan | 0 | — | 92 | 6 |
| | | L-Tyrosine | trace | | | |
| | | L-Phenylalanine | 158 | | | |
| 5 | No. 4 | L-Tryptophan | 0 | L-Tryptophan | | |
| | | L-Tyrosine | trace | 0 | 87 | 6 |
| | | L-Phenylalanine | 158 | 1 | 85 | 8 |
| | | | | 3 | 70 | 20 |
| 6 | No. 4 | L-Tryptophan | 0 | L-Tyrosine | | |
| | | L-Tyrosine | 5 | 5 | 85 | 5 |
| | | L-Phenylalanine | 8 | 8 | 80 | 10 |
| | | | | 10 | 75 | 18 |

TABLE 2-continued

| Run | Lot of CSL used (from Table-2) | Amounts (mg/l) of aromatic amino acids fed to medium containing 26 g/l of CSL | Amount of amino acid added (mg/l) | Output of D—ribose (mg/ml) | Output of gluconic acid (mg/ml) |
| --- | --- | --- | --- | --- | --- |
| 6 | No. 4 | L-Tryptophan<br>L-Tyrosine<br>L-Phenylalanine | L-Phenylalanine<br>0<br>100<br>200 | 87<br>85<br>70 | 6<br>10<br>20 |

It is, thus, clear that by controlling the concentrations of aromatic amino acids in the medium, the output of gluconic acid, which would otherwise amount to about 30–50 mg/ml, can be suppressed to about 5–20 mg/ml while the output of D-ribose is increased.

EXAMPLE 1

*Bacillus pumilus* No. 716 (IFO 13322, FERM BP-812, ATCC 21951) was used to inoculate a medium (10 l) composed of 2% sorbitol, 2% corn steep liquor (Lot No. 4 in Table 1), 0.3% potassium monohydrogen phosphate and 0.1% potassium dihydrogen phosphate and aerobic stirring culture was carried out at 36° C. for 24 hours. This seed culture was used to inoculate a medium (100 l) composed of 20% D-glucose, 2.6% corn steep liquor (Lot No. 4 in Table 1), 0.7% ammonium sulfate, 2.0% calcium carbonate and 0.005% manganese sulfate and aerobic stirring culture (aeration 100 l/min., 210 r.p.m.) was carried out at 38° C. for 55 hours, whereby 92.1 mg/ml of D-ribose was accumulated. This D-ribose fermentation broth was filtered to remove the cells and the filtrate was concentrated to about half the initial volume. To the concentrate was added about ¼ volume of ethanol and after the precipitate was removed, the solution was desalted on a cation and an anion exchange resin and, then, decolorized by a passage through a column of activated carbon. The decolorized effluent was concentrated and about 4 volumes of ethanol was added to the concentrate to give 8.4 kg crystals of D-ribose. In contrast, when cultivation was carried out using CSL Lot No. 1 in Table 1 in the same manner, the output of D-ribose after 55 hours was as low as 6 kg.

EXAMPLE 2

*Bacillus pumilus* No. 716 (IFO 13322, FERM BP-812, ATCC 21951) was used to inoculate 10 l of a medium composed of 2% sorbitol, 2% corn steep liquor (Lot No. 4 in Table 1), 0.3% potassium monohydrogen phosphate and 0.1% potassium dihydrogen phosphate and aerobic stirring culture was carried out at 37° C. for 24 hours. This seed culture was used to inoculate a medium (100 l) composed of 22% D-glucose, 2.6% corn steep liquor (Lot No. 4 in Table 1), 0.5% ammonium sulfate, 2.0% calcium carbonate and 0.005% manganese sulfate and aerobic stirring culture (aeration 100 l/min., 210 r.p.m.) was carried out at 40° C. for 72 hours. The output of D-ribose at the end of the above time period was 90.6 mg/ml. This fermentation broth was treated in the same manner as Example 1 to give 8.3 kg crystals of D-ribose. In contrast, when cultivation was carried out using 2.6% of corn steep liquor (Lot No. 4 in Table 1) and adding 0.001% of L-tyrosine under otherwise the same conditions, the output of D-ribose after 57 hours was as low as 5.6 kg.

EXAMPLE 3

*Bacillus pumilus* No. 716 (IFO 13322, FERM BP-812, ATCC 21951) was used to inoculate a medium (10 l) composed of 2% sorbitol, 2% corn steep liquor (Lot No. 4 in Table 1), 0.3% potassium monohydrogen phosphate and 0.1% potassium dihydrogen phosphate and aerobic stirring culture was carried out at 37° C. for 24 hours. This seed culture was used to inoculate a medium (100 l) composed of 20% D-glucose, 2.6% corn steep liquor (Lot No. 4 in Table 1), 0.5% ammonium sulfate, 2.0% calcium carbonate and 0.005% manganese sulfate and aerobic stirring culture (aeration 100 l/min., 210 r.p.m.) was carried out at 37° C. for 72 hours. The output of D-ribose at the end of the above cultivation time was 95.2 mg/ml. This fermentation broth was treated in the same manner as Example 1 to give 8.5 kg crystals of D-ribose. When cultivation was carried out using 2.6% of corn steep liquor Lot No. 4 and adding 0.01% of phenylalanine under otherwise the same conditions, the output of D-ribose was 87 mg/ml, which yielded 8.3 kg crystals of D-ribose. In contrast, when cultivation was carried out using 2.6% of corn steep liquor Lot No. 4 and adding 0.001% of L-tyrosine under otherwise the same conditions, the output of D-ribose after 57 hours was 5.6 kg.

REFERENCE EXAMPLE

Yellow corn from U.S.A. were steeped in 0.15% sulfur dioxide water in an amount of 1.2 times (v/w) per 1 ton at 35° C. for 48 hours and the grain were separated by the known-method, thereby the corn steep water (CSW) having the following formulation was obtained.

| Total nitrogen (TN) | 0.94% |
| --- | --- |
| NH$_3$—N/TN | 2.7% |
| pH | 4.1 |
| Reducing sugars (RS) | 2.0% |
| Dry solid (DS) | 10.0% |

By aging the obtained CSW (30 l) for 24 hours while keeping at 45° C., the NH$_3$-N/TN, RS and pH changed to 4.6%, 0.8% and 3.8, respectively.

After adjusting the pH to 4.4 by adding 28% NaOH aqueous solution, the CSW was digested under slowly stirring for 25 hours while keeping at 45° C. until the NH$_3$-N/TN was 7.5%. Then after adjusting the pH 4.2 by adding 35% HCl, the CSW was stirred for 47 hours at 45° C. until digested under slowly stirring the NH$_3$-N/TN was about 12.2% and the digestion was stopped by adjusting the pH to 4.0 by adding 35% HCl.

The obtained CSW was concentrated up to about 50% under the reduced pressure to obtain the CSL (7.0 l) having the following formulation.

| TN | 4.0% |
| --- | --- |

| | |
|---|---|
| NH₃—N/TN | 11.9% |
| RS | 0.7% |
| DS | 49.4% |

The amount of tyrosine in the CSL based on wet substance 100 g) was less than 1 mg.

What is claimed is:

1. A process for producing D-ribose which consists essentially of cultivating a D-ribose-producing microorganism of the genus Bacillus in a medium containing nutrients necessary for its growth, wherein the concentrations of L-tryptophan and L-tyrosine in the medium are controlled at 3 μg/ml or less and 10 μg/ml or less, respectively, and harvesting the D-ribose produced and accumulated thereby from the medium.

2. The process according to claim 1, wherein the microorganism is *Bacillus pumilus*.

3. The process according to claim 1, wherein the microorganism is *Bacillus pumilus* No. 716 (FERM BP-812).

4. The process according to claim 1, wherein the concentrations of L-tryptophan and L-tyrosine are 1 μg/ml or less and 5 μg/ml or less, respectively.

5. The process according to claim 1, wherein the concentration of L-phenylalanine in the medium is controlled within the range of 50 to 400 μg/ml.

6. The process according to claim 5, wherein the concentration is 100 to 200 μg/ml.

7. The process according to claim 1, wherein corn steep liquor which does not contain L-typtophan and contains about 0.04% (w/w) or less of L-tyrosine and about 0.5 to 0.7% (w/w) of L-phenylalanine based on the corn steep liquor with water content of 50% is used at the level of about 2 to 2.5% (w/w) based on the total amount of the medium as a nitrogen source.

* * * * *